United States Patent
Wakai et al.

(10) Patent No.: US 12,414,787 B2
(45) Date of Patent: Sep. 16, 2025

(54) ENERGY TREATMENT TOOL

(71) Applicant: OLYMPUS CORPORATION, Tokyo (JP)

(72) Inventors: Hiroshi Wakai, Tokyo (JP); Keisuke Tsurimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1265 days.

(21) Appl. No.: 17/163,758

(22) Filed: Feb. 1, 2021

(65) Prior Publication Data

US 2021/0145469 A1  May 20, 2021

Related U.S. Application Data

(63) Continuation of application No. PCT/JP2018/029182, filed on Aug. 3, 2018.

(51) Int. Cl.
*A61B 17/29*   (2006.01)
*A61B 17/32*   (2006.01)
(Continued)

(52) U.S. Cl.
CPC ...... *A61B 17/29* (2013.01); *A61B 2017/2936* (2013.01); *A61B 17/320092* (2013.01); *A61B 18/085* (2013.01); *A61B 18/1445* (2013.01)

(58) Field of Classification Search
CPC ............ A61B 17/29; A61B 17/320092; A61B 18/085; A61B 18/1445; A61B 2017/2936; A61B 2017/2926

See application file for complete search history.

(56) References Cited

U.S. PATENT DOCUMENTS

2003/0065358 A1* 4/2003 Frecker .................. A61B 17/29
                                                         606/205
2009/0272784 A1* 11/2009 Farascioni ....... A61B 17/07207
                                                         227/176.1
(Continued)

FOREIGN PATENT DOCUMENTS

EP   2781195 A1   9/2014
EP   3138522 A1   3/2017
(Continued)

OTHER PUBLICATIONS

International Search Report dated Oct. 16, 2018 issued in PCT/JP2018/029182.

*Primary Examiner* — Jing Rui Ou
(74) *Attorney, Agent, or Firm* — Scully, Scott, Murphy & Presser, P.C.

(57) ABSTRACT

An energy treatment tool includes: a first gripping piece and second gripping piece that are coupled so as to be relatively opened and closed, the first and second gripping pieces respectively having a first gripping surface and a second gripping surface that are opposed to each other in a closed state and treating, by energy, living tissue gripped between the first and second gripping surfaces; and an alignment part that is provided on the first and second gripping pieces and that aligns the first and second gripping surfaces with each other in a process of closing the first and second gripping pieces, wherein at least one of the first and second gripping surfaces includes a treatment surface that emits energy, and the alignment part is provided at a position other than the treatment surface.

2 Claims, 18 Drawing Sheets

(51) Int. Cl.
*A61B 18/08* (2006.01)
*A61B 18/14* (2006.01)

(56) References Cited

U.S. PATENT DOCUMENTS

| | | | |
|---|---|---|---|
| 2010/0057083 A1 | 3/2010 | Hanna | |
| 2014/0021240 A1 | 1/2014 | Miyamoto | |
| 2014/0100600 A1* | 4/2014 | Kendrick | A61B 17/2841 |
| | | | 606/205 |
| 2014/0336698 A1* | 11/2014 | Boudreaux | A61B 18/00 |
| | | | 606/206 |
| 2015/0190160 A1* | 7/2015 | Kappel | A61B 17/29 |
| | | | 606/207 |
| 2017/0065331 A1 | 3/2017 | Mayer et al. | |
| 2019/0029746 A1* | 1/2019 | Dudhedia | A61B 17/29 |

FOREIGN PATENT DOCUMENTS

| | | |
|---|---|---|
| JP | 2002-085420 A | 3/2001 |
| JP | 2017-047198 A | 3/2017 |
| WO | WO 2013/073523 A1 | 5/2013 |

* cited by examiner

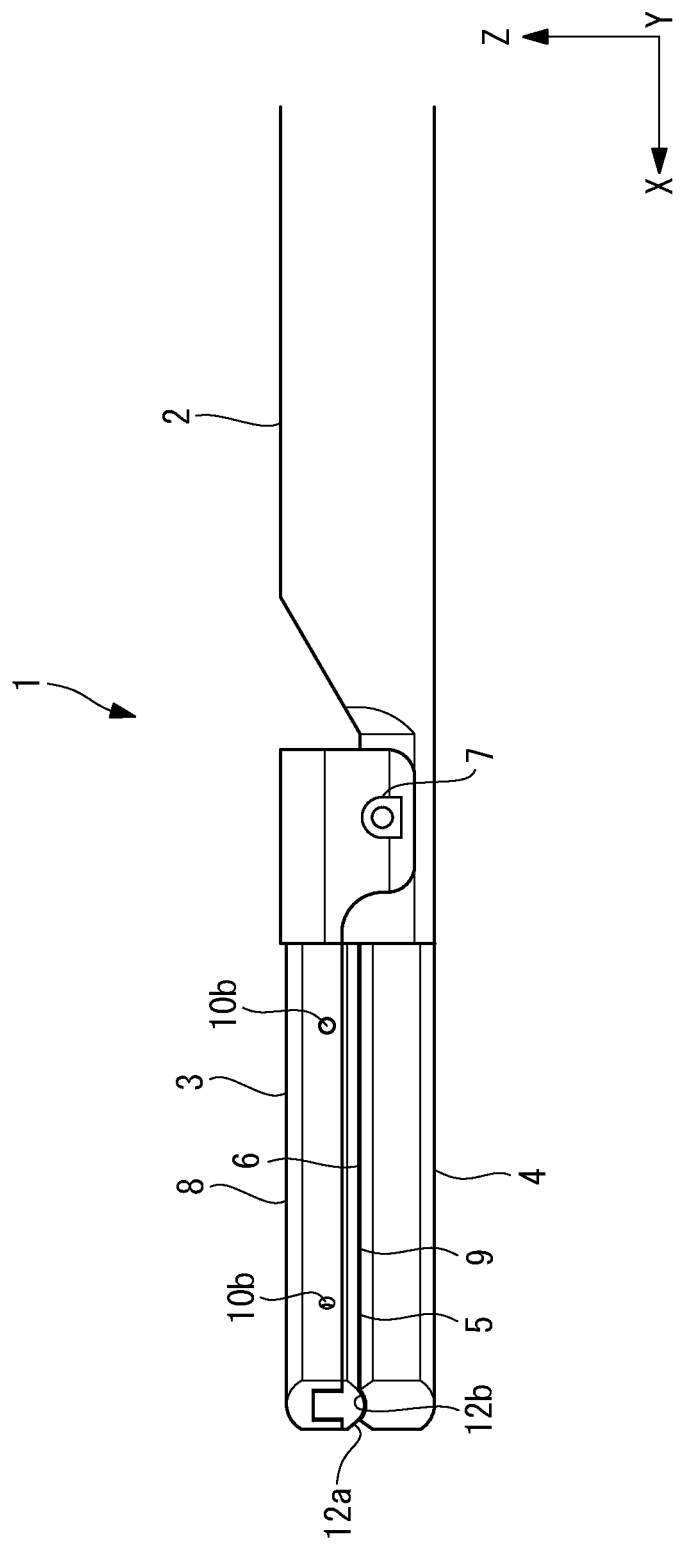

ENERGY TREATMENT TOOL

CROSS-REFERENCE TO RELATED APPLICATIONS

This is a continuation of International Application PCT/JP2018/029182 which is hereby incorporated by reference herein in its entirety.

TECHNICAL FIELD

The present invention relates to an energy treatment tool.

BACKGROUND ART

In the related art, there is known medical equipment that includes a pair of gripping pieces capable of being opened and closed (for example, see PTL 1). A wobble occurs in a pair of gripping pieces coupled by a link or the like. Due to this wobble, when the pair of gripping pieces are closed, relative misalignment could occur in the pair of gripping pieces. In order to prevent misalignment, the medical equipment of PTL 1 includes a positioning part that positions the pair of gripping pieces at a predetermined relative position. For example, in PTL 1, the pair of gripping pieces are positioned by using a combination of a protrusion and a hole that are fitted to each other or a biasing member.

CITATION LIST

Patent Literature

{PTL 1} PCT International Publication No. WO 2013/073523

SUMMARY OF INVENTION

According to one aspect, the present invention provides an energy treatment tool including: a first gripping piece and a second gripping piece that are coupled so as to be relatively opened and closed, the first gripping piece and the second gripping piece respectively having a first gripping surface and a second gripping surface that are opposed to each other in a closed state and treating, by energy, living tissue gripped between the first gripping surface and the second gripping surface; and an alignment part that is provided on the first gripping piece and the second gripping piece and that aligns the first gripping surface and the second gripping surface with each other in a process of closing the first gripping piece and the second gripping piece, wherein at least one of the first gripping surface and the second gripping surface includes a treatment surface that emits energy, and the alignment part is provided at a position other than the treatment surface.

BRIEF DESCRIPTION OF DRAWINGS

FIG. 1B is a side view of the energy treatment tool shown in FIG. 1A, showing a state in which the pair of jaws are closed.

DESCRIPTION OF EMBODIMENT

An energy treatment tool 1 according to one embodiment of the present invention will be described below with reference to the drawings.

Figure 1A:
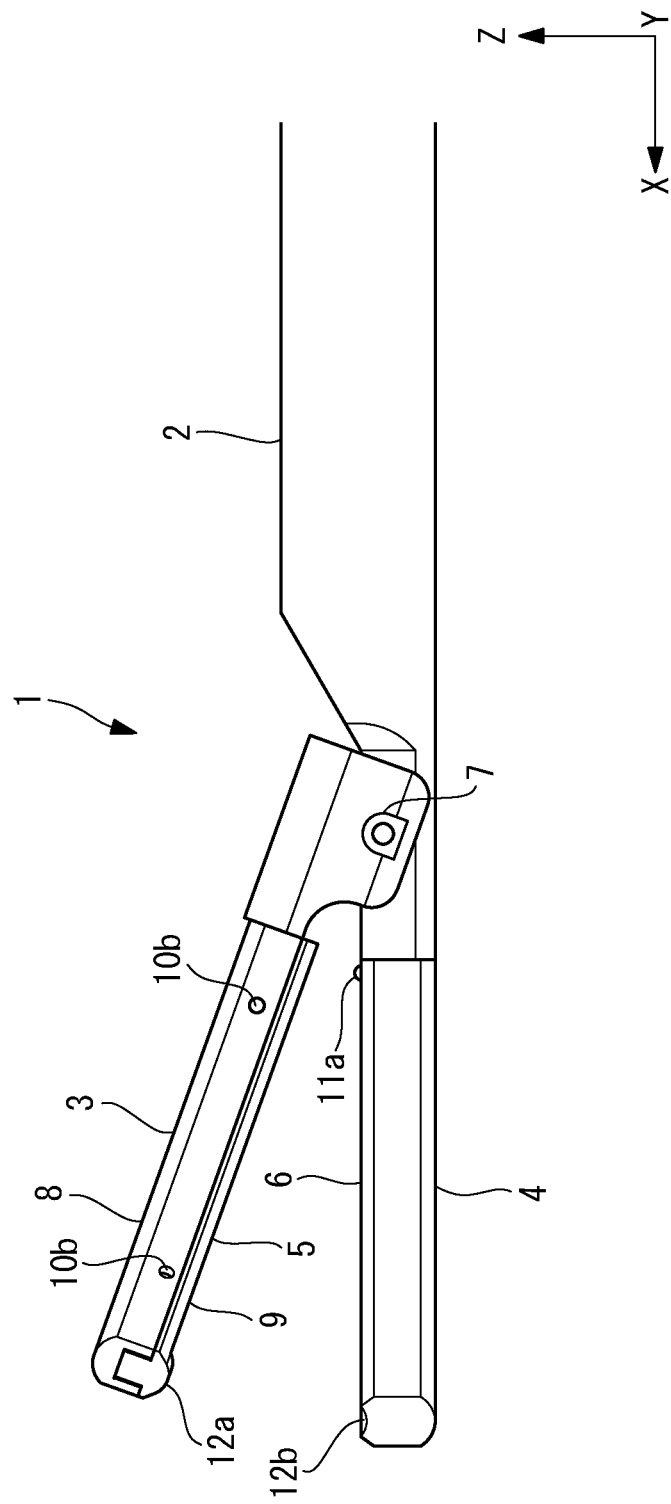
FIG. 1A is a side view of a distal-end section of an energy treatment tool according to one embodiment of the present invention, showing a state in which a pair of jaws are opened.

As shown in FIGS. 1A and 1B, the energy treatment tool 1 of this embodiment includes: a long shaft 2; and an upper jaw (first gripping piece) 3 and a lower jaw (second gripping piece) 4 that are connected to a distal end of the shaft 2. FIG. 1A shows a state in which the jaws 3 and 4 are opened, and FIG. 1B shows a state in which the jaws 3 and 4 are closed.

In the following description, the X-direction is a direction extending along the longitudinal axis of the shaft 2, the Y-direction and the Z-direction are directions that are each perpendicular to the X-direction and that are perpendicular to each other.

The upper jaw 3 and the lower jaw 4 are arrayed in the Z-direction. The upper jaw 3 and the lower jaw 4, which are shown in FIG. 1A to FIG. 7, each have a curve shape curved in a substantially arc manner along a plane in the Y-direction. The upper jaw 3 and the lower jaw 4 may each have a straight shape extending in the X-direction. A proximal-end section of the upper jaw 3 and a proximal-end section of the lower jaw 4 are coupled by a coupling portion 7 so as to be able to mutually swivel about a swivel axis extending in the Y-direction. The coupling portion 7 includes, for example, a hole that penetrates the proximal-end sections of the jaws 3 and 4 in the Y-direction and a pin that is inserted into the hole.

The upper jaw 3 and the lower jaw 4 are relatively opened and closed in the Z-direction (opening and closing directions) by swiveling about the swivel axis. In the drawings to be referred to, the lower jaw 4 is fixed to the shaft 2, and the upper jaw 3 swivels with respect to the lower jaw 4, whereby the jaws 3 and 4 are opened and closed. The upper jaw 3 swivels according to power transmitted to the upper jaw 3 from an operation unit (not shown) connected to a proximal end of the shaft 2, for example, via the coupling portion 7.

Figure 2:
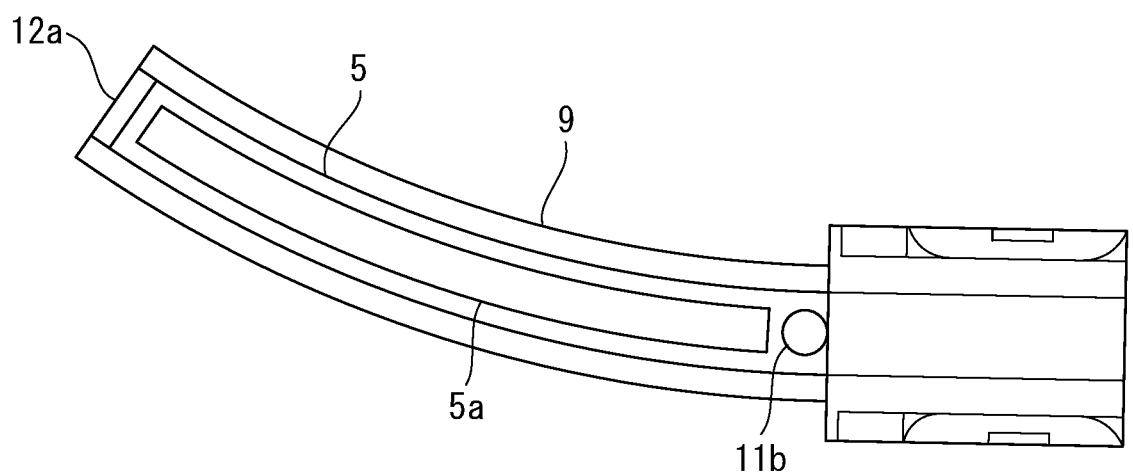
FIG. 2 is a bottom view of an upper jaw viewed from an upper-gripping-surface side.

The upper jaw 3 has an upper gripping surface (first gripping surface) 5, and the lower jaw 4 has a lower gripping surface (second gripping surface) 6. The upper gripping surface 5 and the lower gripping surface 6 are opposed to each other in the Z-direction in a state in which the jaws 3 and 4 are closed. As shown in FIG. 2, a treatment surface 5a that emits energy is provided on the upper gripping surface 5. Similarly, a treatment surface 6a (see FIGS. 12 and 13) that emits energy is provided on the lower gripping surface 6.

Figure 3:
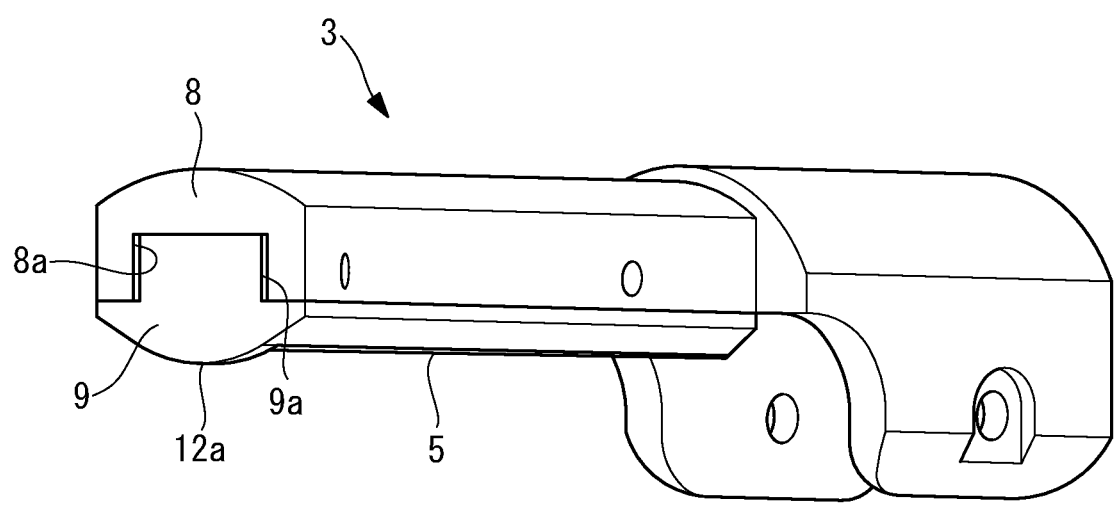
FIG. 3 is a perspective view of the upper jaw.

As shown in FIG. 3, the upper jaw 3 includes: a body 8 that is coupled to the lower jaw 4 by the coupling portion 7; and a movable member 9 that is disposed at the lower jaw 4 side of the body 8 and that has the upper gripping surface 5. The upper jaw 3 is formed by combining the body 8 and the movable member 9 in the Z-direction.

The body 8 has, at a side thereof close to the movable member 9, a rail groove 8a extending in the longitudinal direction.

Figure 4:
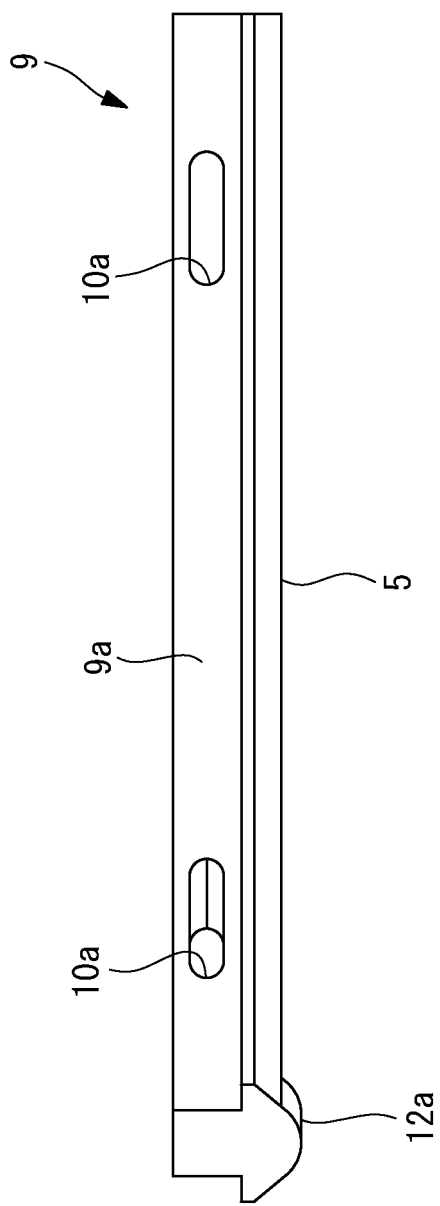
FIG. 4 is a perspective view of a movable member of the upper jaw.
Figure 5:
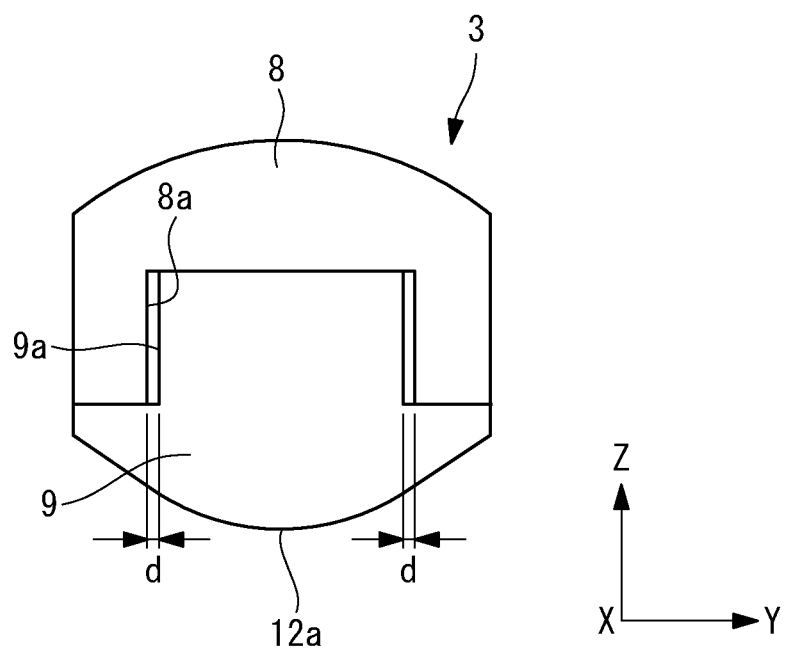
FIG. 5 is a view showing a distal-end surface of a body and the movable member of the upper jaw.

As shown in FIG. 4, the movable member 9 has, at a side thereof close to the lower jaw 4, the upper gripping surface 5 and has, at a side thereof close to the body 8, a rail 9a that protrudes in the Z-direction and that extends in the longitudinal direction. The rail 9a is disposed inside the rail groove 8a so as to be movable in the longitudinal direction. As shown in FIG. 5, the width dimension of the rail 9a in the Y-direction is less than the width dimension of the rail groove 8a in the Y-direction, thus forming a gap d in the Y-direction between an inner surface of the rail groove 8a and an outer surface of the rail 9a.

The body 8 supports the movable member 9 so as to be movable in the X-direction, the Y-direction, and a θ-direction. The θ-direction is a rotation direction in an X-Y plane. As a support mechanism that movably supports the movable member 9, long holes 10a and pins 10b are provided in the upper jaw 3. Specifically, the long holes 10a, which extend in the longitudinal direction of the rail 9a, are provided in the rail 9a. The long holes 10a penetrate through the movable member 9 in the Y-direction. The pins 10b, which extend in the Y-direction, are fixed to the body 8, and the pins 10b are inserted into the long holes 10a. The pins 10b can be moved inside the long holes 10a in the X-direction and the Y-direction.

The rail 9a abuts against the inner surface of the rail groove 8a in the Z-direction and slides in the XY-directions along the rail groove 8a. Specifically, the body 8 supports the movable member 9 so as to be immovable in the Z-direction. The movable member 9 is supported by the long holes 10a and the pins 10b at two places separated from each other in the longitudinal direction. A distal end and a proximal end of the movable member 9 are movable in the directions opposite to each other in the Y-direction, thus allowing the movable member 9 to rotate in the θ-direction.

It is also possible to form the long holes 10a in the body 8 and to fix the pins 10b to the movable member 9.

A first alignment part 11 and a second alignment part 12 for aligning the upper gripping surface 5 with respect to the lower gripping surface 6 in the process of closing the jaws 3 and 4 are provided on the upper jaw 3 and the lower jaw 4.

The first alignment part 11 is used to align the upper gripping surface 5 with respect to the lower gripping surface 6 in the X-direction and the Y-direction and is provided at the proximal-end sections of the jaws 3 and 4.

The second alignment part 12 is used to align the upper gripping surface 5 with respect to the lower gripping surface 6 in the θ-direction and is provided at the distal-end sections of the jaws 3 and 4.

Figure 6:
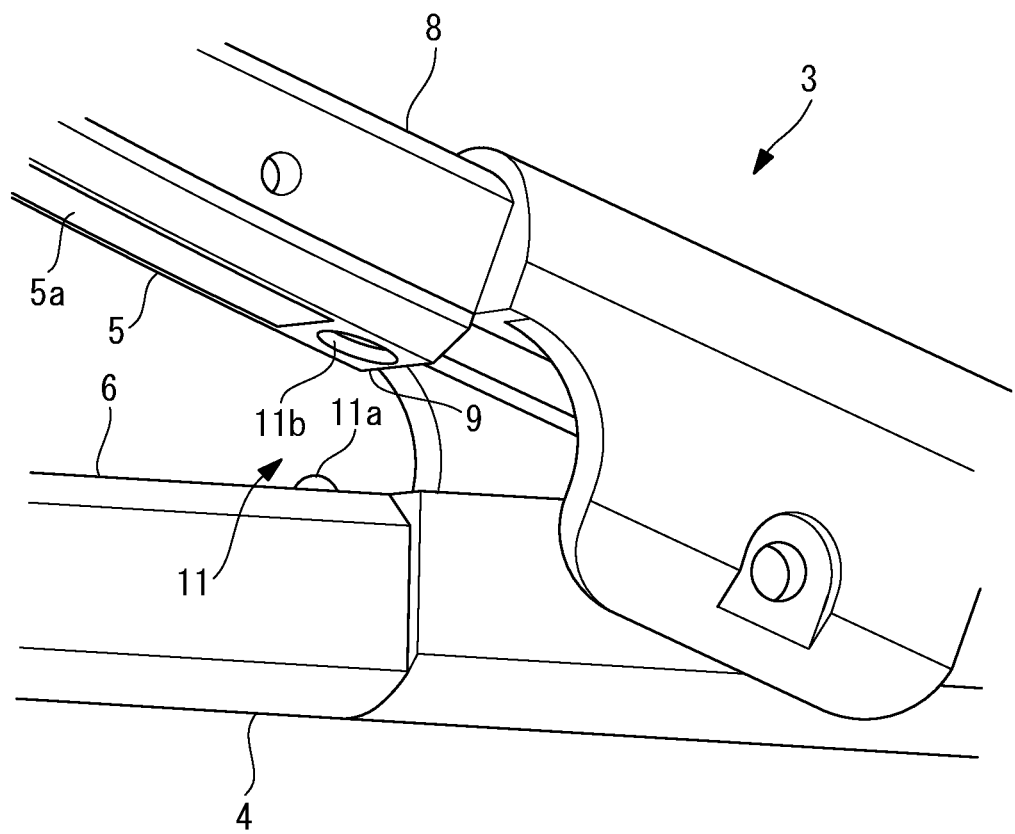
FIG. 6 is an enlarged view of proximal-end sections of the pair of jaws, showing a first alignment part.

As shown in FIG. 6, the first alignment part 11 includes: a protruding part 11a that is provided on a proximal-end section of the lower gripping surface 6 and that protrudes from the lower gripping surface 6 in the Z-direction; and a recessed part 11b that is provided in a proximal-end section of the upper gripping surface 5 and that receives the protruding part 11a in the Z-direction. The protruding part 11a has a substantially hemispherical shape, and the recessed part 11b has a substantially hemispherical shape. The protruding part 11a and the recessed part 11b may have shapes other than hemispherical shapes.

Figure 8:
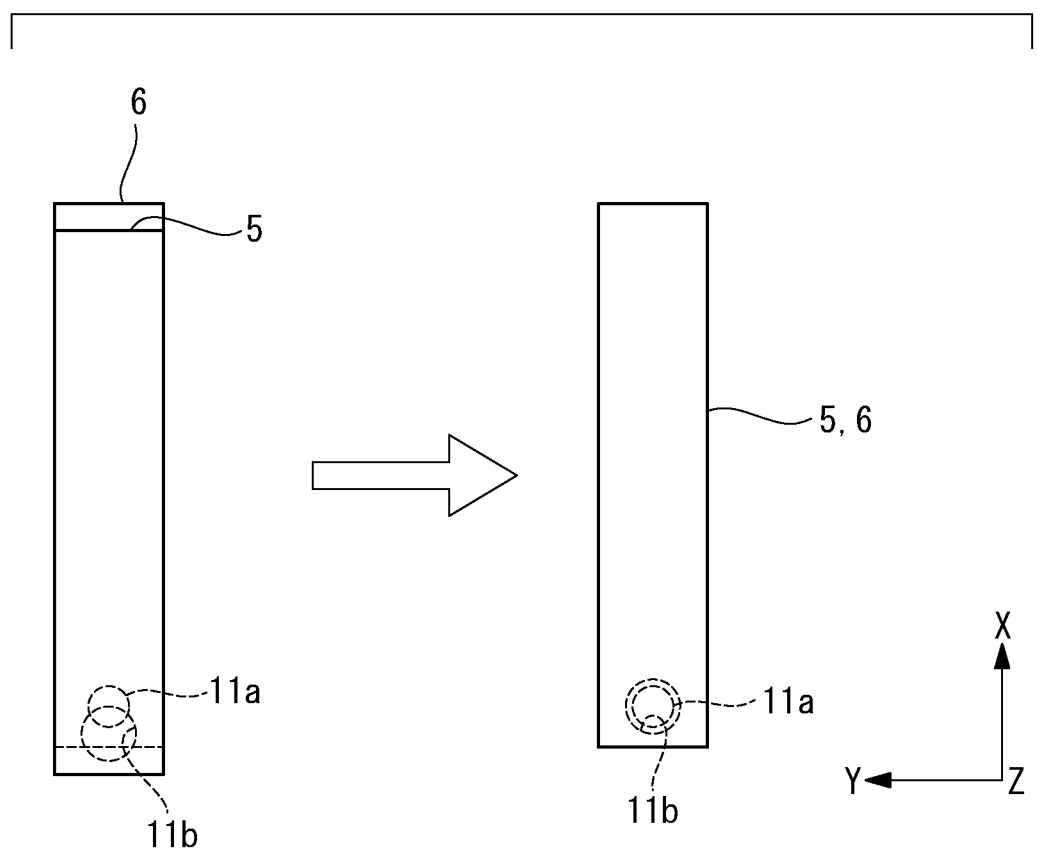
FIG. 8 is a view for explaining an alignment operation of a pair of straight-shaped jaws in the X-direction performed by using the first alignment part.
Figure 9:
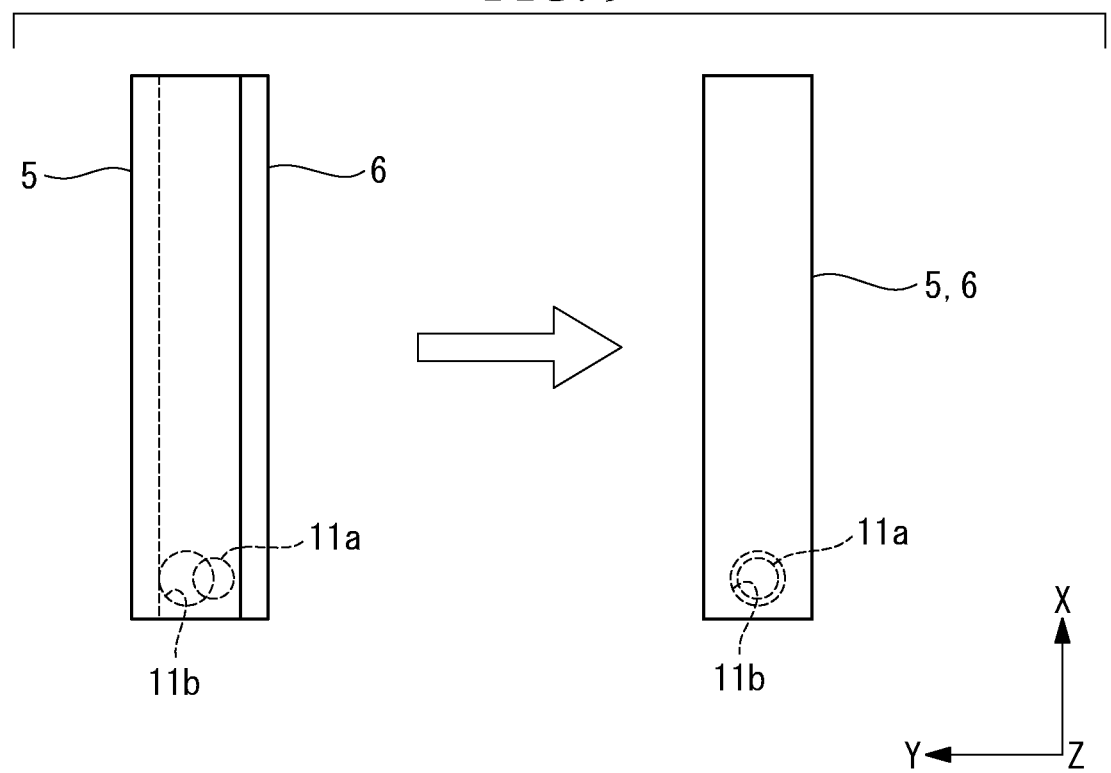
FIG. 9 is a view for explaining an alignment operation of the pair of straight-shaped jaws in the Y-direction performed by using the first alignment part.
Figure 11:
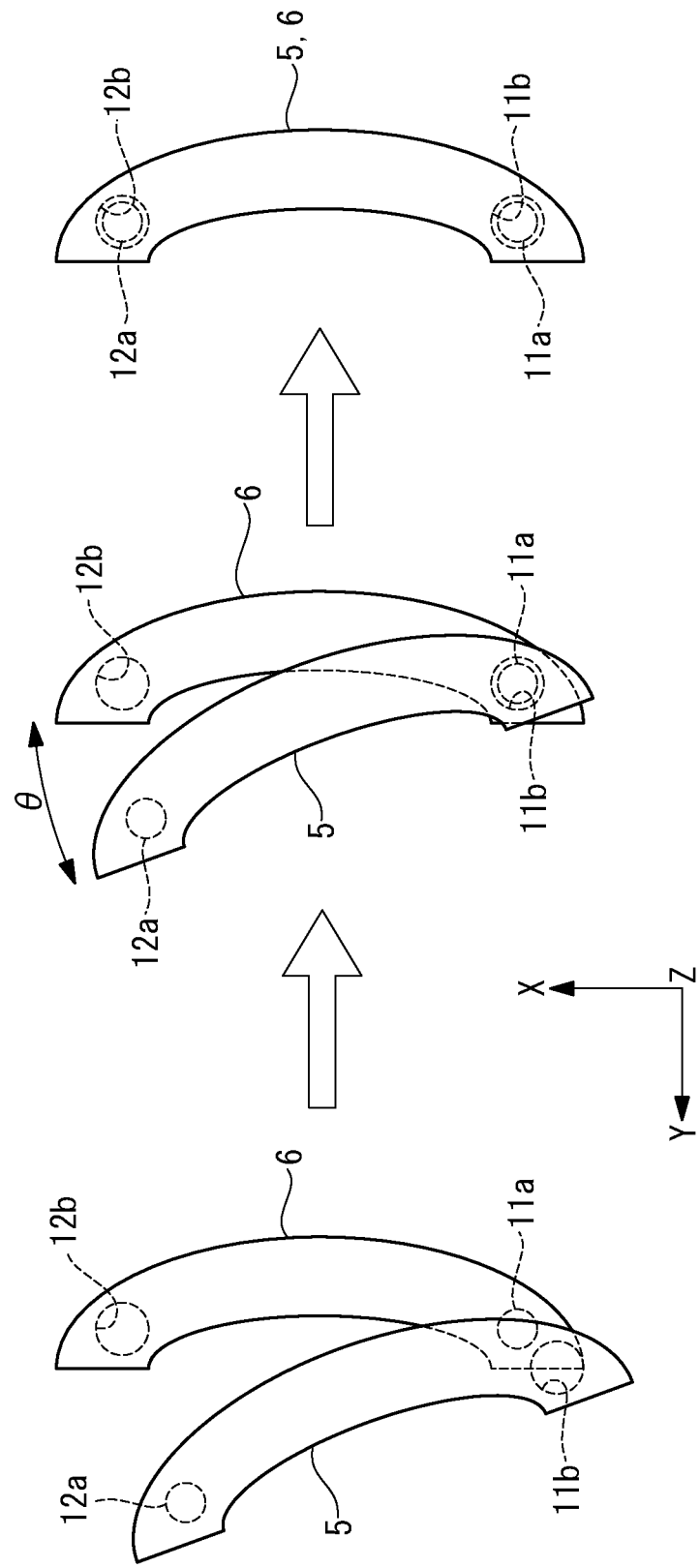
FIG. 11 is a view for explaining an alignment operation of a pair of curve-shaped jaws in the X-direction, the Y-direction, and the θ-direction performed by using the first and second alignment parts.

The recessed part 11b has larger dimensions than the protruding part 11a in the X-direction and the Y-direction, so that the protruding part 11a and the recessed part 11b are fitted to each other in a state in which the treatment surface 5a and the treatment surface 6a perfectly overlap each other in the Z-direction. Therefore, as shown in FIGS. 8 and 11, in the process of closing the jaws 3 and 4, through movement of the movable member 9 in the X-direction, the upper gripping surface 5 is aligned with respect to the lower gripping surface 6 in the X-direction, at the position where the protruding part 11a is fitted into the recessed part 11b. Similarly, as shown in FIGS. 9 and 11, in the process of closing the jaws 3 and 4, through movement of the movable member 9 in the Y-direction, the upper gripping surface 5 is aligned with respect to the lower gripping surface 6 in the Y-direction, at the position where the protruding part 11*a* is fitted into the recessed part 11*b*. FIGS. 8 and 9 show alignment operations of straight-shaped jaws 3 and 4, and FIG. 11 shows an alignment operation of curve-shaped jaws 3 and 4.

Figure 7:
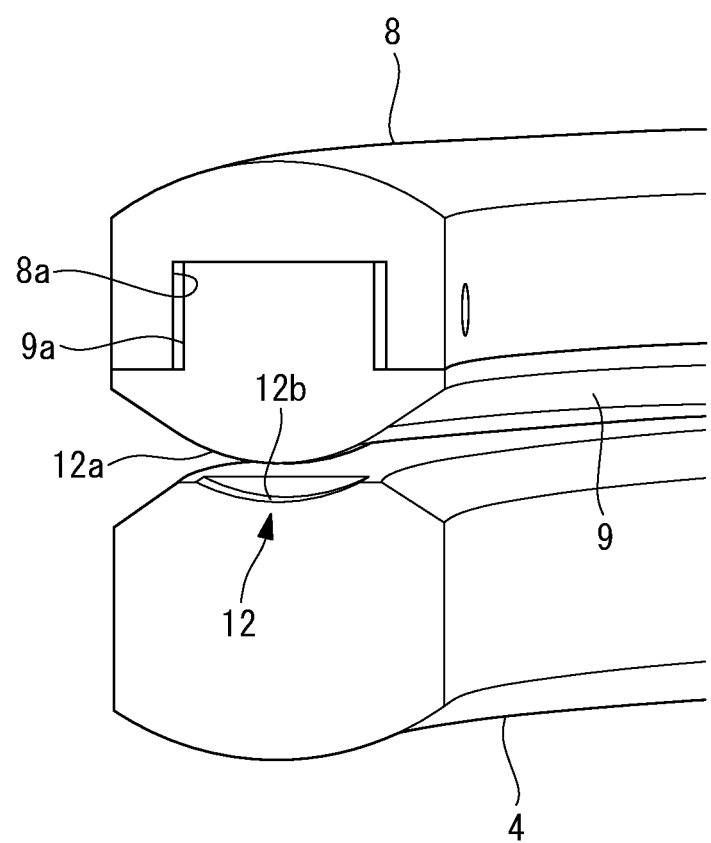
FIG. 7 is an enlarged view of distal-end sections of the pair of jaws, showing a second alignment part.
Figure 10:
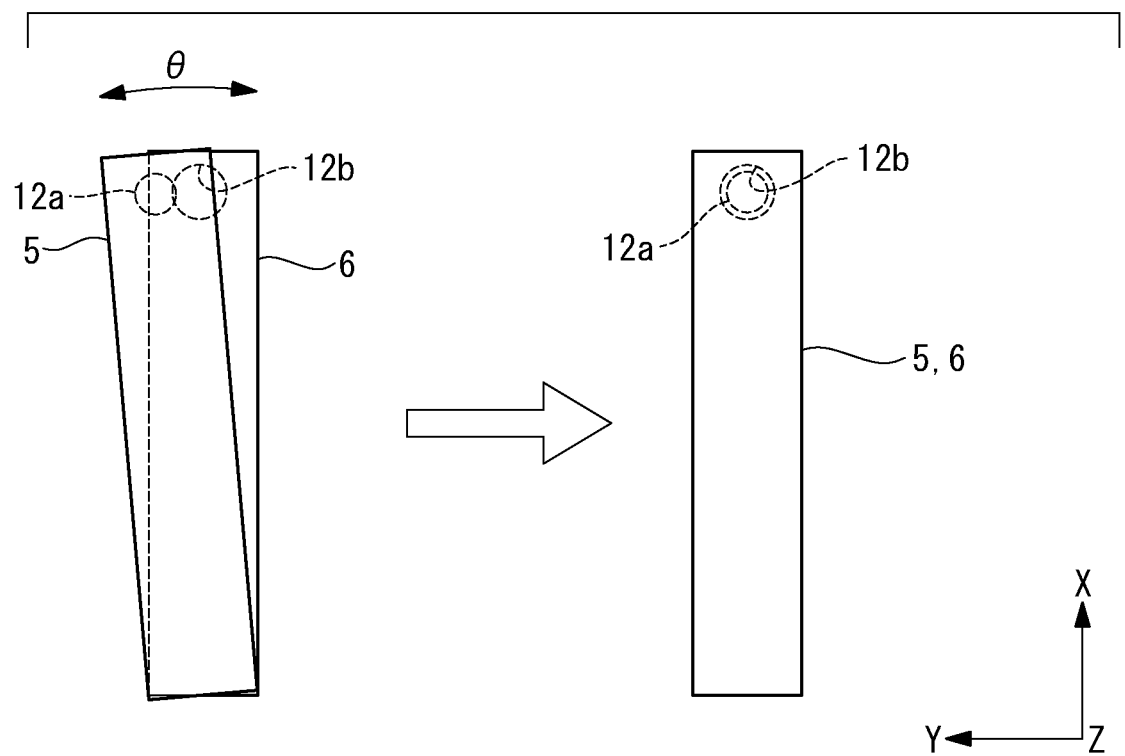
FIG. 10 is a view for explaining an alignment operation of the pair of straight-shaped jaws in the θ-direction performed by using the second alignment part.

As shown in FIG. 7, the second alignment part 12 includes: a protruding part 12*a* that is provided at a distal-end section of the upper gripping surface 5 and that protrudes from the upper gripping surface 5 in the Z-direction; and a recessed part 12*b* that is provided in a distal-end section of the lower gripping surface 6 and that receives the protruding part 12*a* in the Z-direction. An end face of the protruding part 12*a* close to the lower jaw 4 has an arc shape protruding toward the lower jaw 4, when viewed in the X-direction. The protruding part 12*a* has a plate shape or a spherical shape. The recessed part 12*b* has an inner-surface shape complementary to the outer-surface shape of the protruding part 12*a*. The protruding part 12*a* and the recessed part 12*b* are fitted to each other in a state in which the treatment surface 5*a* and the treatment surface 6*a* perfectly overlap each other in the Z-direction. Therefore, as shown in FIGS. 10 and 11, in the process of closing the jaws 3 and 4, through movement of the movable member 9 in the θ-direction, the upper gripping surface 5 is aligned with respect to the lower gripping surface 6 in the θ-direction, at the position where the protruding part 12*a* is fitted into the recessed part 12*b*. FIG. 10 shows an alignment operation of the straight-shaped jaws 3 and 4.

The amounts of protrusion of the protruding parts 11*a* and 12*a* are designed such that, in the process of closing the jaws 3 and 4, the protruding part 11*a* and the recessed part 11*b* of the first alignment part 11 are fitted to each other, and then the protruding part 12*a* and the recessed part 12*b* of the second alignment part 12 are fitted to each other.

It is preferred that the first alignment part 11 be provided at a position other than the treatment surface 5*a*, in order to prevent the first alignment part 11 from interfering with living tissue sandwiched between the treatment surfaces 5*a* and 6*a*. Similarly, it is preferred that the second alignment part 12 be provided at a position other than the treatment surface 6*a*, in order to prevent the second alignment part 12 from interfering with living tissue sandwiched between the treatment surfaces 5*a* and 6*a*. In the example shown in FIGS. 6 and 7, the first alignment part 11 (11*a*, 11*b*) and the second alignment part 12 (12*a*, 12*b*) are provided in regions secured at both sides of the treatment surfaces 5*a* and 6*a* in the X-direction. As another example arrangement of the alignment parts 11 and 12, the alignment parts 11 and 12 may be provided in regions secured at outer sides of the treatment surfaces 5*a* and 6*a* in the Y-direction.

Next, the operation of the thus-configured energy treatment tool 1 will be described below.

In order to treat living tissue by using the energy treatment tool 1 of this embodiment, the living tissue is sandwiched between the pair of opened jaws 3 and 4, and the pair of jaws 3 and 4 are closed, thereby gripping the living tissue between the treatment surfaces 5*a* and 6*a*. Next, energy is emitted from the treatment surfaces 5*a* and 6*a* and is supplied to the living tissue between the treatment surfaces 5*a* and 6*a*. The energy is, for example, high frequency, heat, or ultrasound. An energy source for causing the energy to be emitted is supplied to the treatment surfaces 5*a* and 6*a*, for example, via an energy transmission member that connects the treatment surfaces 5*a* and 6*a* and the operation unit. The living tissue is heated by the energy, thereby achieving treatment, such as joining, hemostasis, cauterization, or the like.

In this case, in the process of closing the jaws 3 and 4, the upper gripping surface 5 is aligned with respect to the lower gripping surface 6 in two steps. Specifically, through movement of the movable member 9 in the X-direction and the Y-direction with respect to the body 8, the upper gripping surface 5 is aligned with respect to the lower gripping surface 6 in the X-direction and the Y-direction, at the position where the recessed part 11*b* is fitted to the outer side of the protruding part 11*a*. Then, when the jaws 3 and 4 are further closed, through movement of the movable member 9 with respect to the body 8 in the θ-direction, the upper gripping surface 5 is aligned with respect to the lower gripping surface 6 in the θ-direction, at the position where the protruding part 12*a* is fitted to the inner side of the recessed part 12*b*. As a result of the two-step alignment, the gripping surfaces 5 and 6 are aligned with each other at the position where the treatment surfaces 5*a* and 6*a* perfectly or almost perfectly overlap each other in the Z-direction.

In order that the upper jaw 3 can swivel with respect to the lower jaw 4, it is necessary to secure a gap between the body 8 of the upper jaw 3 and the lower jaw 4, at the coupling portion 7. Due to this gap, a wobble occurs in the upper jaw 3, thus causing a shift in the position of the upper jaw 3 with respect to the lower jaw 4 in a state in which the jaws 3 and 4 are closed, in some cases. According to this embodiment, there is an advantage in that, irrespective of the presence or absence of a wobble, the upper gripping surface 5 can be aligned by the alignment parts 11 and 12 with respect to the lower gripping surface 6 at a predetermined position where the treatment surfaces 5*a* and 6*a* overlap each other in the Z-direction.

Furthermore, the upper gripping surface 5 is provided on the movable member 9, which is separate from the body 8 coupled to the lower jaw 4, and the movable member 9 is movable with respect to the body 8. According to this configuration, alignment of the upper gripping surface 5 with respect to the lower gripping surface 6 is achieved through movement of the movable member 9, while the position of the body 8 with respect to the lower jaw 4 is maintained. Specifically, in the alignment of the gripping surfaces 5 and 6, a situation in which a force is applied to the coupling portion 7 is prevented, and a change in the coupled state of the jaws 3 and 4 at the coupling portion 7 is prevented. Accordingly, there is an advantage in that it is possible to prevent a reduction in the efficiency of power transmission to the upper jaw 3 and a reduction in the gripping force caused thereby. In the energy treatment tool 1, for which a high gripping force is particularly required, it is possible to reduce friction occurring at the coupling portion 7 and to improve durability.

The above-described two-step alignment of the gripping surfaces 5 and 6 is particularly effective when the jaws 3 and 4 have curve shapes, as shown in FIG. 11.

When the jaws 3 and 4 have curve shapes, it is necessary to entirely align the jaws 3 and 4 with each other from the distal-end sections to the proximal-end sections. If the jaws 3 and 4 are shifted at the proximal-end sections in the X-direction and the Y-direction, misalignment between the gripping surfaces 5 and 6 becomes large, so that the treatment surfaces 5*a* and 6*a* do not overlap each other in the Z-direction. The first alignment part 11 aligns the proximal-end sections of the gripping surfaces 5 and 6 in the X-direction and the Y-direction, and then the second alignment part 12 aligns the distal-end sections of the gripping surfaces 5 and 6 in the θ-direction, thereby making it possible to accurately align the curved treatment surfaces 5a and 6a with each other.

Figure 12:
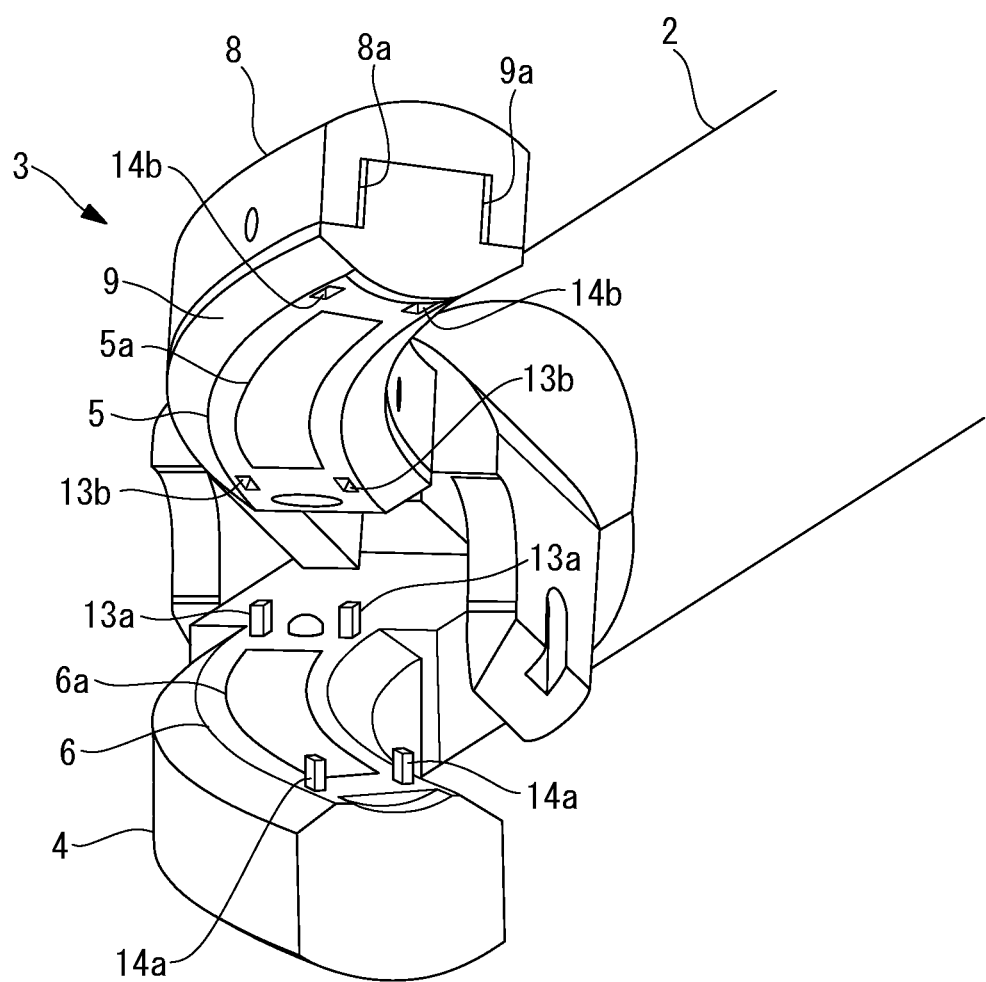
FIG. 12 is a view showing a modification of the first and second alignment parts.
Figure 13:
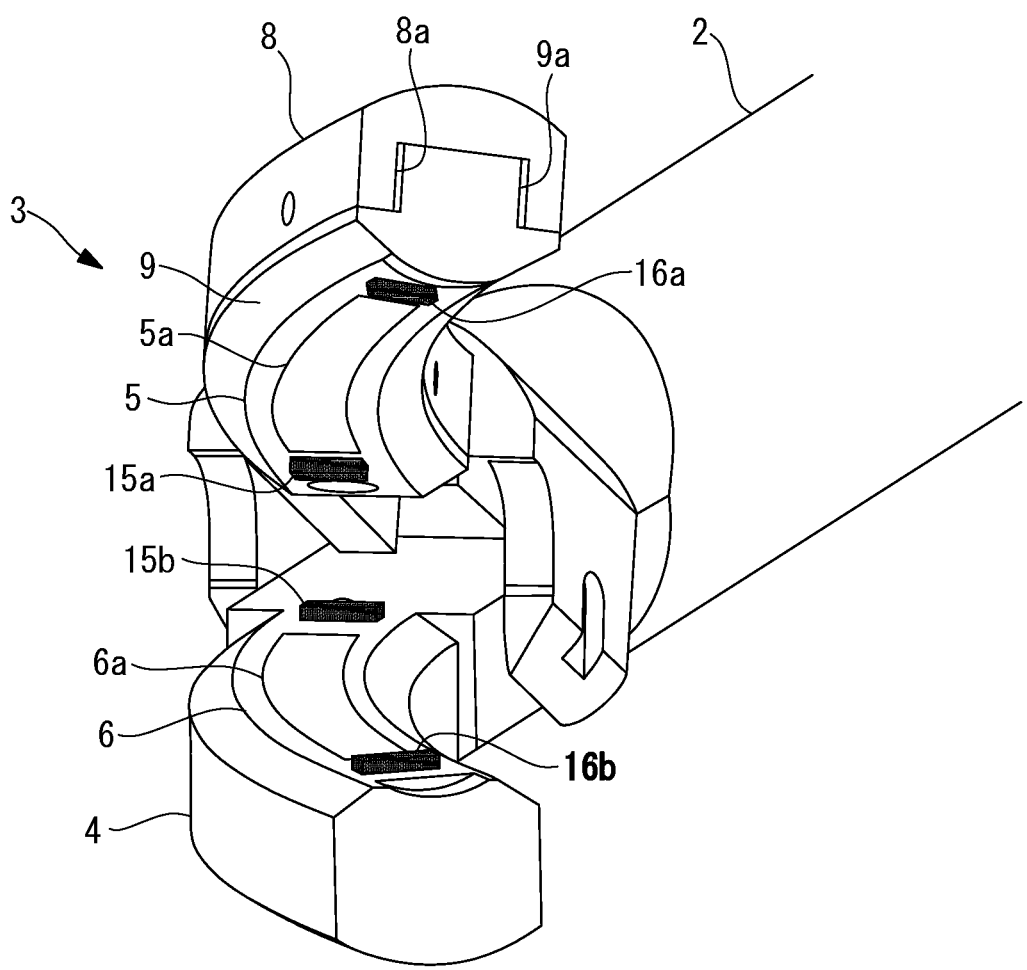
FIG. 13 is a view showing another modification of the first and second alignment parts.

In this embodiment, the alignment parts 11 and 12 are not limited to the above-described combinations of the protruding parts 11a and 12a and the recessed parts 11b and 12b, respectively, and can be appropriately modified. FIGS. 12 and 13 show modifications of the alignment parts.

In FIG. 12, the first alignment part 11 is formed of a combination of pins 13a that stand up from the lower gripping surface 6 and holes 13b that are formed in the upper gripping surface 5 and that receive the pins 13a in the Z-direction. It is also possible to form the pins 13a on the upper gripping surface 5 and to form the holes 13b in the lower gripping surface 6. Similarly, the second alignment part 12 is formed of a combination of pins 14a and holes 14b.

In FIG. 13, the first alignment part 11 is formed of a combination of a magnet 15a that is fixed to the upper gripping surface 5 and a magnet 15b that is fixed to the lower gripping surface 6. The magnets 15a and 15b generate magnetic attraction with each other. Similarly, the second alignment part 12 is formed of a combination of magnets 16a and 16b.

Figure 14:
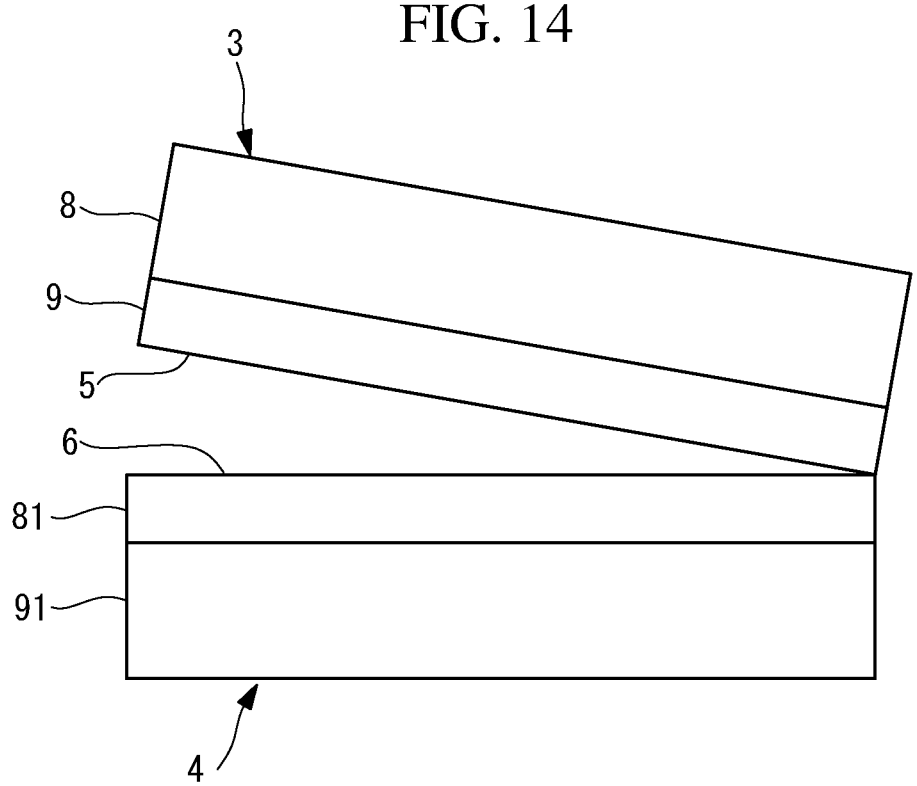
FIG. 14 is a view showing, in outline, the configuration of a modification of the pair of jaws shown in FIG. 1A.

In this embodiment, although only the upper jaw 3 includes the movable member 9, as shown in FIG. 14, the lower jaw 4 may also include a movable member 91 that has the gripping surface 6 and that is movably supported by a body 81.

Figure 15A:
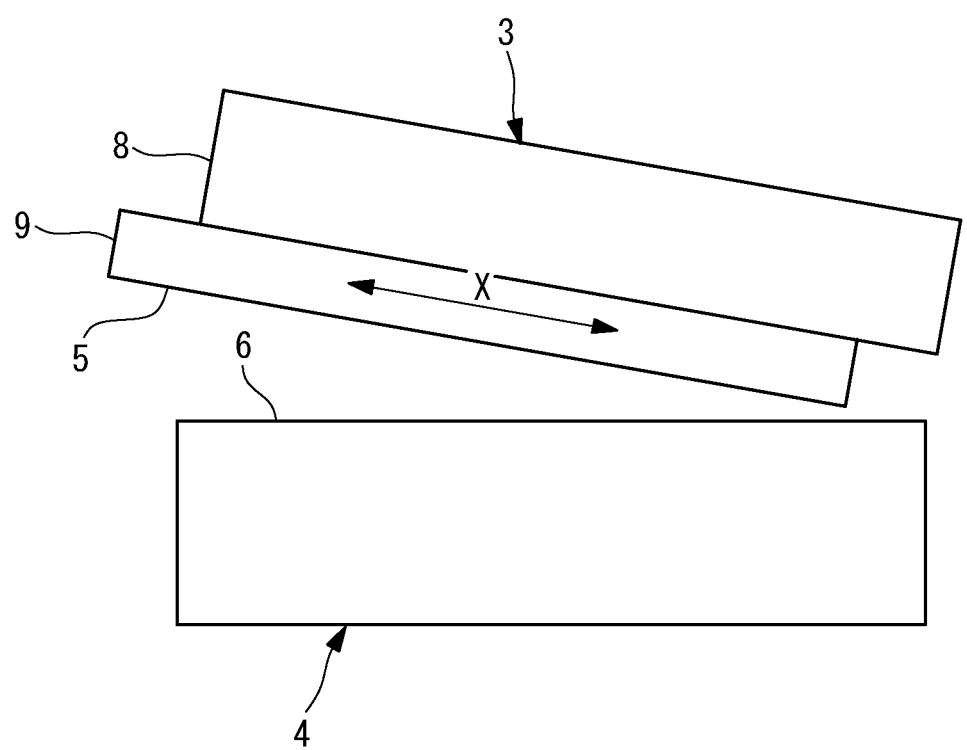
FIG. 15A is a view showing, in outline, the configuration of a modification of the upper jaw shown in FIG. 1A.
Figure 15B:
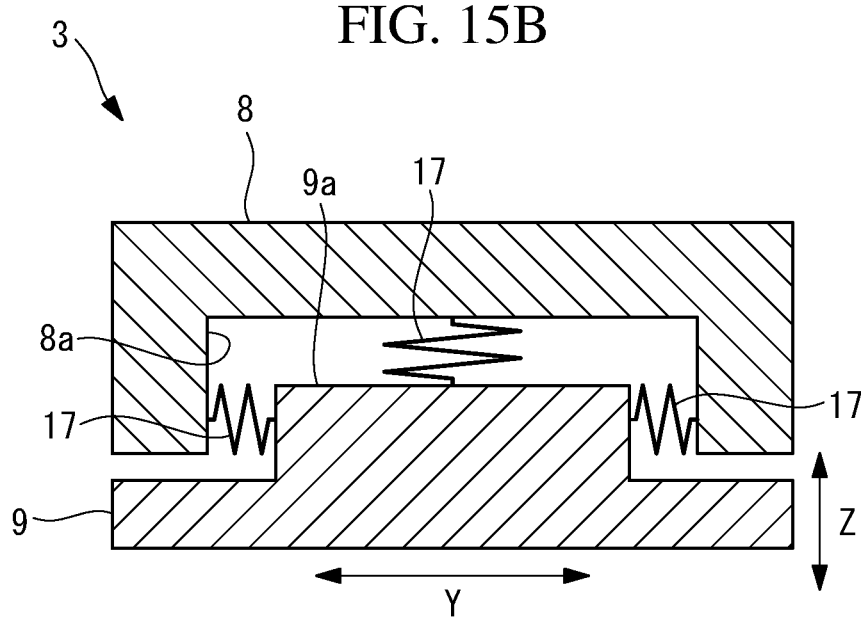
FIG. 15B is a transverse sectional view of an upper jaw shown in FIG. 15A, showing, in outline, the configuration of a modification of a support mechanism.

In this embodiment, as shown in FIGS. 15A and 15B, the movable member 9 may also be supported so as to be movable in the Z-direction, in addition to the X-direction and the Y-direction.

In the modification shown in FIGS. 15A and 15B, the movable member 9 is supported by the body 8 by means of spring-like elastic members 17 so as to be movable in the X-direction, the Y-direction, and the Z-direction. According to this modification, the degree of freedom in the direction of movement of the movable member 9 is increased, thus allowing the movable member 9 to move in arbitrary 3D directions.

Figure 16A:
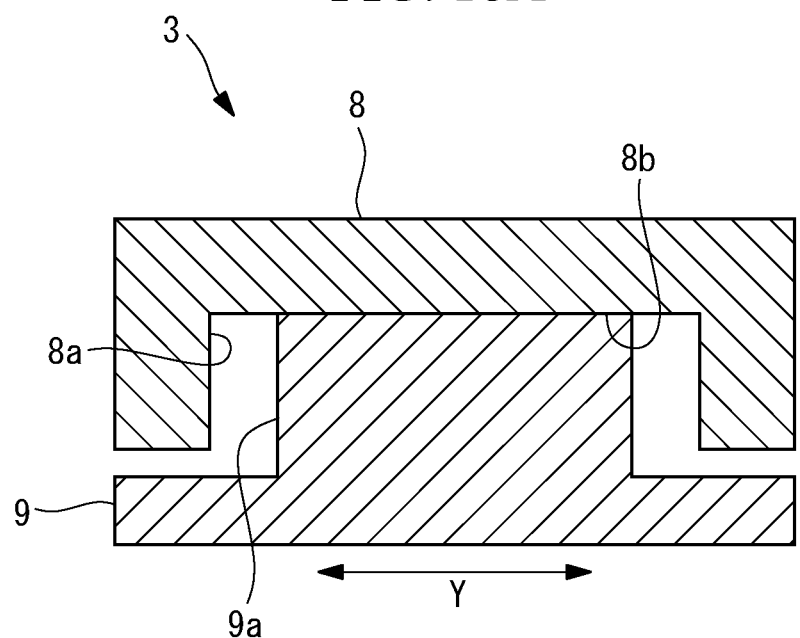
FIG. 16A is a transverse sectional view of another modification of the upper jaw shown in FIG. 1A, showing, in outline, the configuration of another modification of the support mechanism.
Figure 16B:
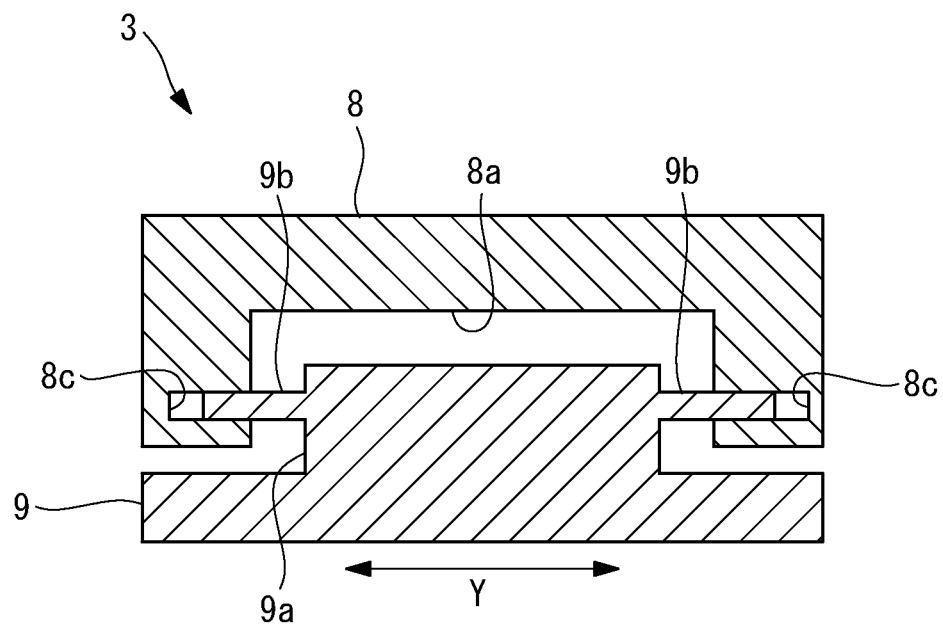
FIG. 16B is a transverse sectional view of still another modification of the upper jaw shown in FIG. 1A, showing, in outline, the configuration of still another modification of the support mechanism.

In this embodiment, it is also possible to provide, on the upper jaw 3, a restriction part that restricts movement of the movable member 9 in a predetermined direction with respect to the body 8. FIGS. 16A and 16B show example restriction parts that restrict movement of the movable member 9 in the Z-direction.

In FIG. 16A, the rail 9a of the movable member 9 abuts against an inner surface 8b of the rail groove 8a in the Z-direction. Specifically, the inner surface 8b functions as a restriction part.

In FIG. 16B, guide members 9b that protrude from the rail 9a toward both sides in the Y-direction are provided on the movable member 9, and guide grooves 8c into which the guide members 9b are inserted are formed in inner surfaces of the rail groove 8a of the body 8. The guide members 9b abut against the inner surfaces of the guide grooves 8c in the Z-direction, thereby restricting movement of the guide members 9b in the Z-direction. Specifically, the guide grooves 8c and the guide members 9b function as restriction parts.

In this embodiment, although the combination of the long holes 10a and the pins 10b is used as the support mechanism, which supports the movable member 9 so as to be movable with respect to the body 8, instead of this, another structure may be used.

Figure 17A:
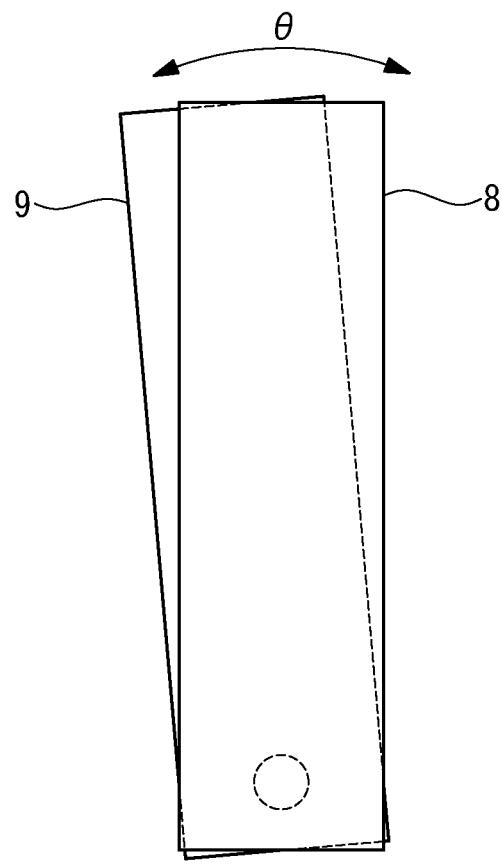
FIG. 17A is a view showing, in outline, the configuration of still another modification of the upper jaw shown in FIG. 1A.
Figure 17B:
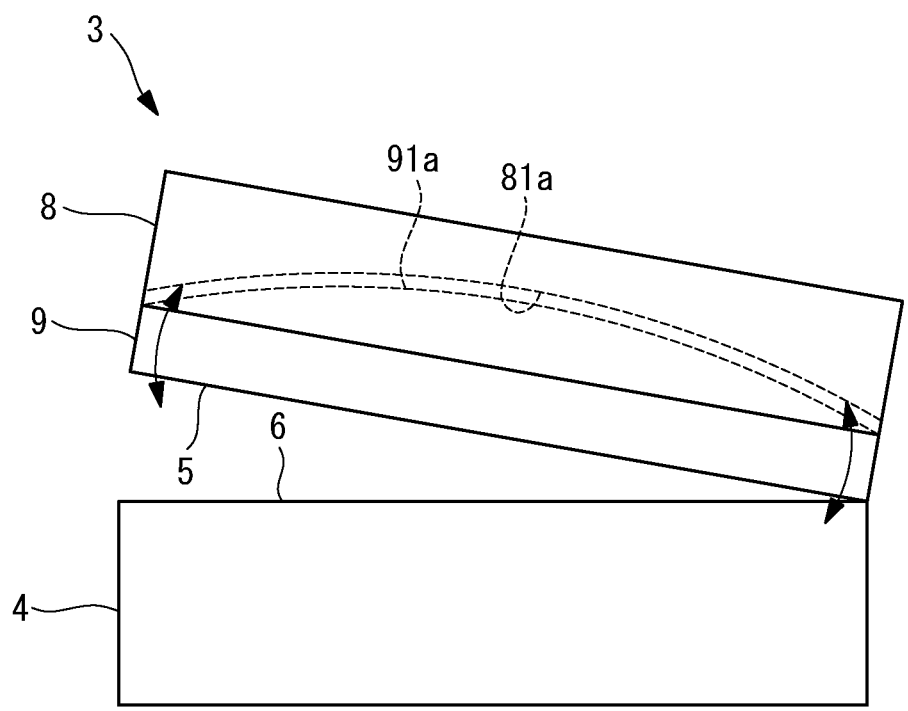
FIG. 17B is a side view of an upper jaw shown in FIG. 17A.
Figure 17C:
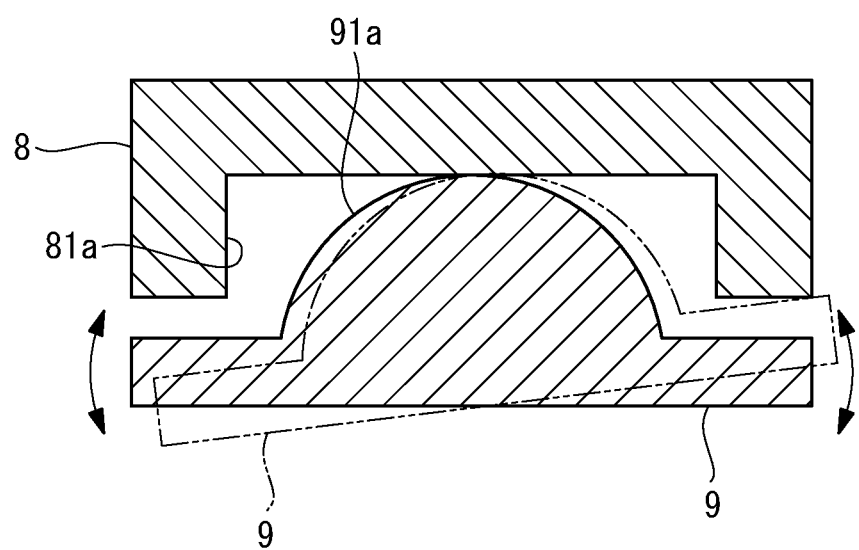
FIG. 17C is a transverse sectional view of the upper jaw shown in FIG. 17A, showing, in outline, the configuration of still another modification of the support mechanism.

FIGS. 17A to 17C show a modification of the support mechanism, which supports the movable member 9 so as to be movable in the θ-direction. An outer surface of a rail 91a is a curved surface that has curvature in the X-direction and the Y-direction and that protrudes toward the body 8. As shown in FIG. 17A, the movable member 9 moves in the θ-direction with respect to the body 8 through movement of the rail 91a in the θ-direction inside a rail groove 81a. In this modification, the movable member 9 can swivel about a swivel axis extending in the Y-direction, with respect to the body 8, as shown in FIG. 17B, and can swivel about a swivel axis extending in the X-direction, with respect to the body 8, as shown in FIG. 17C.

FIGS. 18A to 18F show modifications of the support mechanism, which supports the movable member 9 so as to be movable in the X-direction, the Y-direction, and the Z-direction.

Figure 18A:
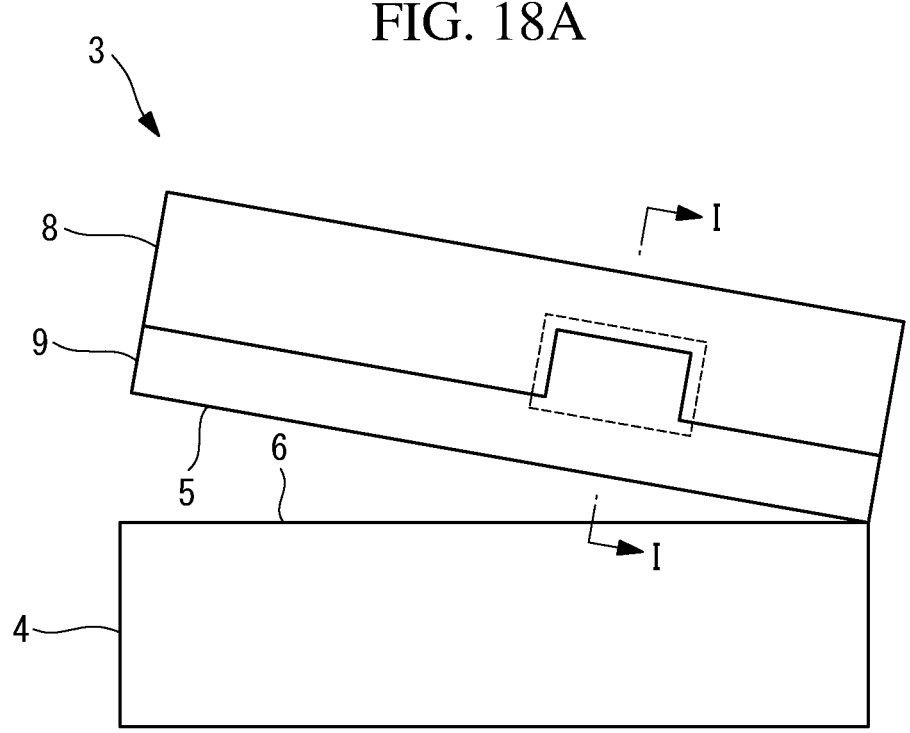
FIG. 18A is a view showing, in outline, the configuration of still another modification of the upper jaw shown in FIG. 1A.

Support mechanisms shown in FIGS. 18B to 18F are each provided between the body 8 and the movable member 9, as shown in FIG. 18A (see the dashed-line rectangular area in FIG. 18A). FIGS. 18B to 18F are transverse sectional views of the upper jaw 3 in the Z-direction.

Figure 18B:
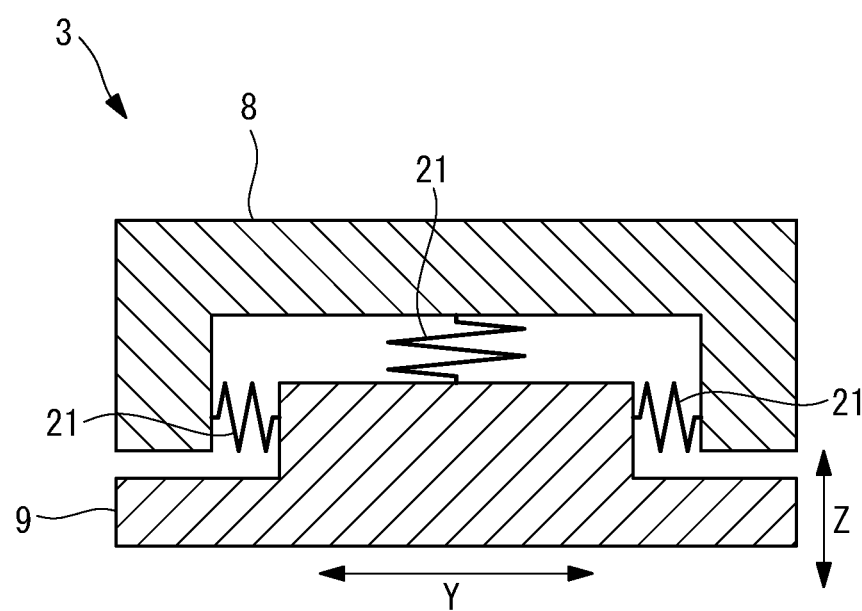
FIG. 18B is a transverse sectional view of an upper jaw shown in FIG. 18A cut along the I-I line and showing, in outline, the configuration of still another modification of the support mechanism.
Figure 18C:
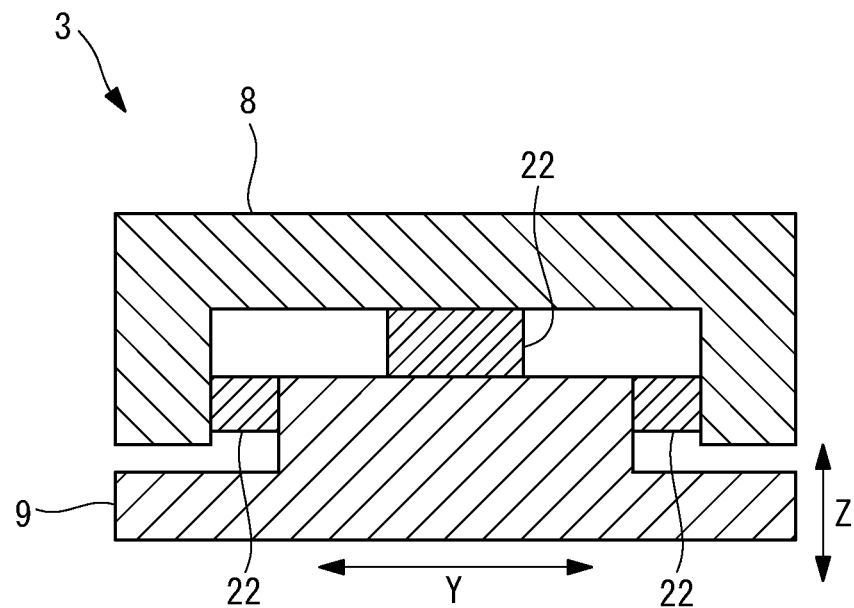
FIG. 18C is a transverse sectional view of the upper jaw shown in FIG. 18A cut along the I-I line and showing, in outline, the configuration of still another modification of the support mechanism.

The body 8 and the movable member 9 are connected by elastic members 21 in FIG. 18B and by elastic members 22 in FIG. 18C. The elastic members 21 are springs in FIG. 18B, and the elastic members 22 are rubber members in FIG. 18C. The movable member 9 can move in the X-direction, the Y-direction, and the Z-direction through expansion and contraction of the elastic members 21 or 22.

Figure 18D:
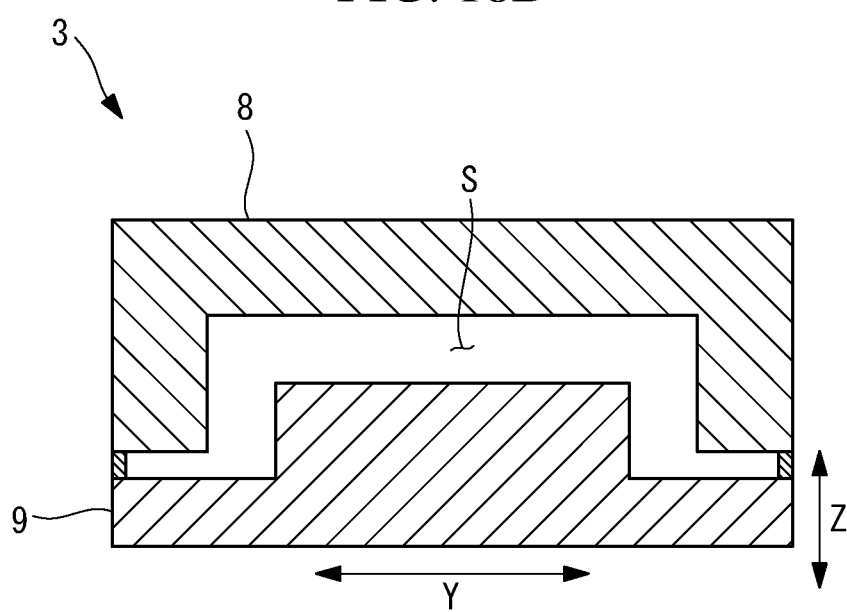
FIG. 18D is a transverse sectional view of the upper jaw shown in FIG. 18A cut along the I-I line and showing, in outline, the configuration of still another modification of the support mechanism.

In FIG. 18D, a closed space S is formed between the body 8 and the movable member 9, and a fluid is filled in the closed space S. The movable member 9 can move in the X-direction, the Y-direction, and the Z-direction through movement of the fluid in the closed space S.

Figure 18E:
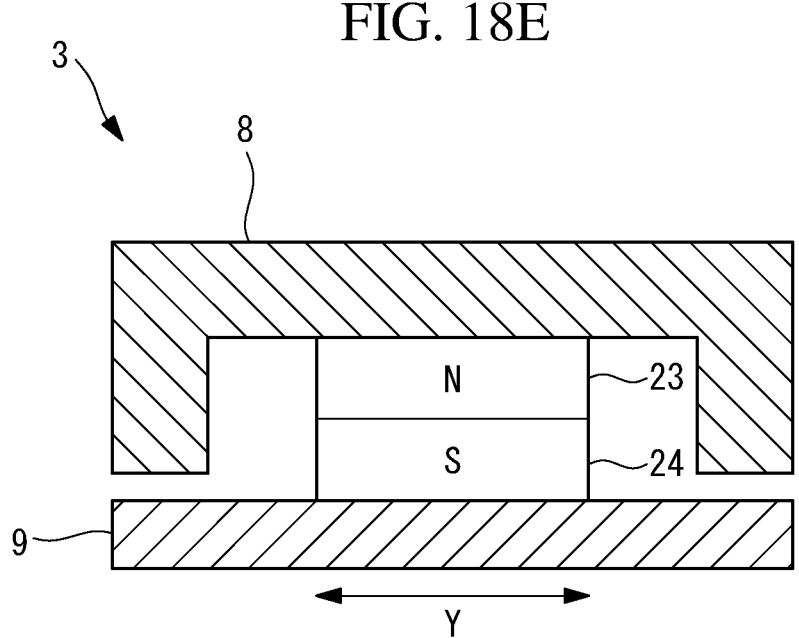
FIG. 18E is a transverse sectional view of the upper jaw shown in FIG. 18A cut along the I-I line and showing, in outline, the configuration of still another modification of the support mechanism.

In FIG. 18E, a magnet 23 is fixed to the body 8, and a magnet 24 is fixed to the movable member 9. The movable member 9 is supported by the body 8 due to magnetic attraction in the Z-direction between the magnets 23 and 24. The magnetic attraction between the magnets 23 and 24 is weaker than the force acting on the movable member 9 in the X-direction and the Y-direction for alignment, thus allowing movement of the movable member 9 in the X-direction and the Y-direction with respect to the body 8.

Figure 18F:
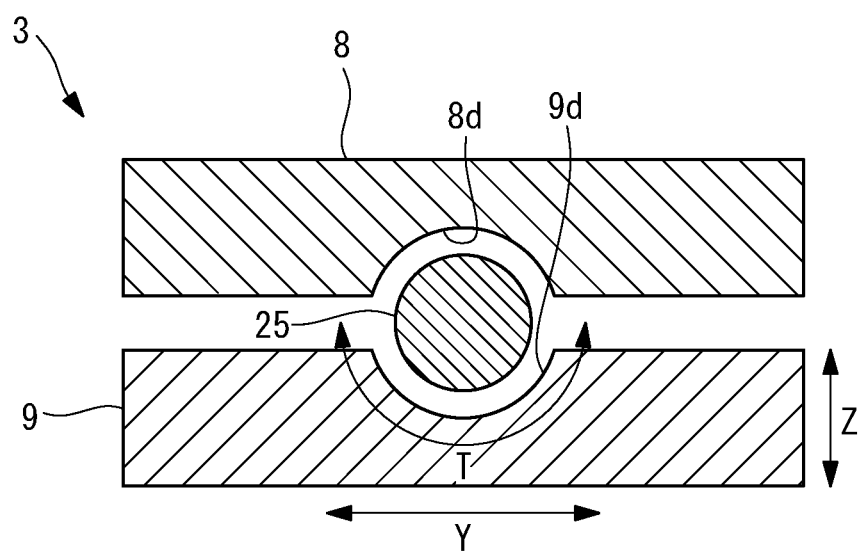
FIG. 18F is a transverse sectional view of the upper jaw shown in FIG. 18A cut along the I-I line and showing, in outline, the configuration of still another modification of the support mechanism.

In FIG. 18F, a spherical ball 25 is disposed between the body 8 and the movable member 9. A substantially hemispherical recessed surface 8d is formed on the body 8, and a substantially hemispherical recessed surface 9d is formed on the movable member 9. The ball 25 is disposed in a substantially spherical space between the recessed surfaces 8d and 9d. The radii of curvature of the recessed surfaces 8d and 9d are larger than the radius of curvature of the ball 25, thus forming a gap between the recessed surfaces 8d and 9d and an outer surface of the ball 25. The movable member 9 can move in the X-, Y-, and Z-directions and, in addition, can swivel in a tilt direction T, with respect to the body 8. The tilt direction T is the direction of rotation about an axis extending in the X-direction. Therefore, through swiveling of the movable member 9 in the tilt direction T, the upper gripping surface 5 can be aligned also in the tilt direction with respect to the lower gripping surface 6.

The above-described embodiment also leads to the following aspects.

According to one aspect, the present invention provides an energy treatment tool including a first gripping piece and a second gripping piece that are coupled so as to be able to be relatively opened and closed, the first gripping piece and the second gripping piece respectively having a first gripping surface and a second gripping surface that are opposed to each other in a closed state and treating, by energy, living tissue gripped between the first gripping surface and the second gripping surface, wherein the first gripping piece includes a movable member having the first gripping surface and movably supports the movable member.

According to this aspect, in a state in which the first gripping piece and the second gripping piece are closed, if the position of the first gripping surface is shifted with respect to the second gripping surface, it is possible to align the first gripping surface with respect to the second gripping surface through movement of the movable member.

In this case, because the movable member is movably supported by the first gripping piece, it is possible to move the first gripping surface while a coupled state of the first gripping piece and the second gripping piece at a coupling portion is maintained. Accordingly, it is possible to align the first gripping piece and the second gripping piece with each other, without reducing the power transmission efficiency.

In the above-described aspect, the first gripping piece may support the movable member so as to be rotatable in a plane intersecting opening and closing directions.

With this configuration, it is possible to align the first gripping surface with respect to the second gripping surface in the rotation direction in the plane.

In the above-described aspect, the first gripping piece and the second gripping piece may be curved in a substantially arc manner in the plane intersecting the opening and closing directions.

In a case in which the first and second gripping pieces are curved, due to small misalignment thereof in the rotation direction, the positions of the first gripping surface and the second gripping surface are significantly shifted. Therefore, in the case in which the first and second gripping pieces are curved, movement of the movable member in the rotation direction is particularly effective in aligning the first gripping surface and the second gripping surface.

In the above-described aspect, the first gripping piece may support the movable member so as to be movable in a direction intersecting opening and closing directions.

With this configuration, it is possible to align the first gripping surface with respect to the second gripping surface in a direction intersecting the opening and closing directions.

In the above-described aspect, the first gripping piece may support the movable member so as to be able to swivel about an axis perpendicular to opening and closing directions.

With this configuration, it is possible to align the first gripping surface with respect to the second gripping surface about an axis perpendicular to the opening and closing directions.

In the above-described aspect, the first gripping piece may support the movable member so as to be immovable in opening and closing directions.

With this configuration, it is possible to more strongly grip living tissue between the first gripping surface and the second gripping surface.

The above-described aspect may further include an alignment part that is provided on the first gripping piece and the second gripping piece and that aligns the first gripping surface and the second gripping surface with each other in a process of closing the first gripping piece and the second gripping piece.

With this configuration, at the time of a closing operation of the first gripping piece and the second gripping piece, the movable member can be moved to a position at which the first gripping surface is aligned with respect to the second gripping surface by the alignment part.

In the above-described aspect, at least one of the first gripping surface and the second gripping surface may include a treatment surface that emits energy; and the alignment part may be provided at a position other than the treatment surface.

The treatment surface is a region where living tissue is disposed. By providing the alignment part at a position other than the treatment surface, the alignment part can be prevented from interfering with the living tissue on the treatment surface.

In the above-described aspect, the alignment part may include: a protruding part that is provided in one of the first gripping surface and the second gripping surface; and a recessed part that is provided in the other one of the first gripping surface and the second gripping surface and that receives the protruding part in a closing direction of the first gripping piece and the second gripping piece.

With a simple configuration formed of a combination of the protruding part and the recessed part, it is possible to realize alignment between the first and second gripping surfaces.

In the above-described aspect, in the process of closing the first gripping piece and the second gripping piece, the alignment part may align the first gripping surface and the second gripping surface in a direction intersecting opening and closing directions and then may align the first gripping surface and the second gripping surface in a rotation direction in a plane intersecting the opening and closing directions.

With this configuration, the first gripping surface and the second gripping surface can be aligned with high accuracy.

In the above-described aspect, the first gripping piece and the second gripping piece may be coupled at one-end sections thereof so as to be able to relatively swivel, the alignment part may include a first alignment part that aligns the first gripping surface and the second gripping surface in a direction intersecting the opening and closing directions and a second alignment part that aligns the first gripping surface and the second gripping surface in the rotation direction, and the first alignment part may be provided at a position closer to the one-end sections than the second alignment part is.

At the time of a closing operation of the first and second gripping pieces by a method for performing opening and closing through swiveling, alignment in a direction intersecting the opening and closing directions is performed by the first alignment part, which is close to the one-end sections, and then alignment in a rotation direction is performed by the second alignment part, which is far from the one-end sections. In this way, the order of the alignment in the aforementioned intersecting direction and the alignment in the rotation direction can be controlled by the positions of the first alignment part and the second alignment part.

In the above-described aspect, the first gripping piece may include a body that is coupled to the second gripping piece, the body movably supporting the movable member; and the first gripping piece may include a long hole that is formed in one of the body and the movable member and a pin that is fixed to the other one of the body and the movable member and that is movably disposed in the long hole.

With this simple configuration formed of a combination of the long hole and the pin, the movable member can be movably supported by the body.

In the above-described aspect, the first gripping piece may include a restriction part that restricts a movement direction of the movable member.

With this configuration, movement of the movable member can be restricted only in an intended direction.

REFERENCE SIGNS LIST 1 energy treatment tool
2 shaft
3 upper jaw (first gripping piece)
4 lower jaw (second gripping piece)
5 upper gripping surface (first gripping surface)
5a treatment surface
6 lower gripping surface (second gripping surface)
6a treatment surface
7 coupling portion
8 body
9 movable member
11 first alignment part
11a protruding part
11b recessed part
12 second alignment part
12a protruding part
12b recessed part

The invention claimed is:

1. An energy treatment tool comprising:
a first gripping piece including a movable member, the first gripping piece movably supporting the movable member, the movable member having a first gripping surface;
a second gripping piece having a second gripping surface facing the first gripping surface; and
an alignment part comprising:
a protrusion provided in one of the first gripping surface and the second gripping surface; and
a recess provided in the other of the first gripping surface and the second gripping surface, the recess configured to receive the protrusion;
wherein the alignment part is provided at one of:
a distal end of the first gripping surface and a distal end of the second gripping surface; or
a proximal end of the first gripping surface and a proximal end of the second gripping surface;
wherein the first gripping piece comprises a body, the body movably supporting the movable member, and
the first gripping piece comprises:
a hole formed in one of the body and the movable member; and
a pin provided to the other of the body and the movable member, the pin is movably disposed in the hole.

2. The energy treatment tool according to claim 1, the hole having a first length and a second length, the first length is a length in a longitudinal direction of the first gripping piece, the second length is a length in a direction intersecting the longitudinal direction of the first gripping piece, the first length is longer than the second length.

* * * * *